(12) United States Patent
Batty et al.

(10) Patent No.: US 6,469,020 B2
(45) Date of Patent: Oct. 22, 2002

(54) HYDROXAMIC AND CARBOXYLIC ACID DERIVATIVES

(75) Inventors: Duncan Batty; Verity Margaret Sabin; Robert John Watson; Hazel Joan Dyke; Andrew Sharpe; Richard John Davenport; David Alan Owen; Andrew Douglas Baxter, all of Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/855,978

(22) Filed: May 15, 2001

(65) Prior Publication Data

US 2002/0013333 A1 Jan. 31, 2002

(30) Foreign Application Priority Data

| May 15, 2000 | (GB) | ................................ 0011720 |
| Mar. 23, 2001 | (GB) | ................................ 0107359 |

(51) Int. Cl.$^7$ .................. A61K 31/4355; A61K 31/437; A61K 31/4365; C07D 471/04; C07D 491/048
(52) U.S. Cl. ...................... 514/290; 514/291; 514/292; 546/85; 546/89
(58) Field of Search .......... 546/81–85, 86–89; 514/290, 291, 292

(56) References Cited

FOREIGN PATENT DOCUMENTS

| EP | 0780386 | 12/1996 |
| WO | 9724117 | 1/1997 |
| WO | 9805635 | 8/1997 |
| WO | 9924399 | 11/1998 |
| WO | 0012477 | 8/1999 |
| WO | 0012478 | 8/1999 |

OTHER PUBLICATIONS

Caplus English abstract DN 120:323955 , Bracher franz et al , 1994, vol. 327 (2).*

Caplus , English Abstract DN 132:334370 J org. Chem. vol. 65, (8) , 2000.*

* cited by examiner

*Primary Examiner*—Alan L. Rotman
*Assistant Examiner*—Rita Desai
(74) *Attorney, Agent, or Firm*—Salinwanchik, Lloyd & Salinwanchik

(57) ABSTRACT

The invention relates to hydroxamic and carboxylic acid derivatives. Compounds of the formula:

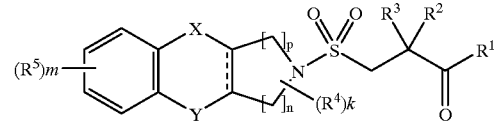

are disclosed. These compounds are useful for the treatment of diseases mediated by inhibitors of matrix metalloproteinase, ADAM, ADAM-TS enzymes, and or INFα-mediated diseases including degenerative diseases and certain cancers.

15 Claims, No Drawings

HYDROXAMIC AND CARBOXYLIC ACID DERIVATIVES

FIELD OF THE INVENTION

This invention relates to hydroxamic and carboxylic acid derivatives, and to their use in medicine.

BACKGROUND TO THE INVENTION

Metalloproteinases, including matrix metalloproteinase (MMP), collagenase, gelatinase and TNFα convertase (TACE), and their modes of action, and also inhibitors thereof and their clinical effects, are described in WO-A-96/11209, WO-A-97/12902 and WO-A-97/19075, the contents of which are incorporated herein by reference. MMP inhibitors may also be useful in the inhibition of other mammalian metalloproteinases such as the ADAM or ADAM-TS families.

Compounds which have the property of inhibiting the action of metalloproteinases involved in connective tissue breakdown, such as collagenase, stromelysin and gelatinase, have been shown to inhibit the release of TNFα both in vitro and in vivo. See Gearing et al (1994), Nature 370:555–557; McGeehan et al (1994), Nature 370:558–561; GB-A-2268934; and WO-A-93/20047. All of these reported inhibitors contain a hydroxamic acid zinc-binding group, as do the imidazole-substituted compounds disclosed in WO-A-95/23790. Other compounds that inhibit MMP and/or TNFα are described in WO-A-95/13289, WO-A-96/11209, WO-A-96/035687, WO-A-96/035711, WO-A-96/035712 and WO-A-96/035714.

SUMMARY OF THE INVENTION

The invention encompasses novel compounds of formula (I) which are inhibitors of matrix metalloproteinase, ADAM or ADAM-TS enzymes, and which are useful for the treatment of diseases mediated by those enzymes and/or TNFα-mediated diseases, including degenerative diseases and certain cancers.

Novel compounds according to a first aspect of the invention are represented by formula (I):

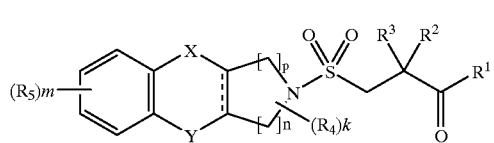

(I)

wherein $R^1$ is OH or NHOH;

$R^2$ is H, alkyl, alkenyl, alkynyl, aryl, arylalkyl, heteroaryl, heteroarylalkyl, cycloalkyl, cycloalkylalkyl, heterocyclo or heterocycloalkyl (any of which may be optionally substituted with one or more substituents selected from $R^6$, W and $WR^6$); and $R^3$ is H or alkyl;

or $R^2$, $R^3$ and the carbon atom to which they are attached together represent a carbocyclic or heterocyclic ring (either of which may be substituted with one or more substituents selected from $R^6$, W and $WR^6$);

$R^4$ is alkyl, cycloalkyl, $OR^9$, $CO_2R^{14}$, $COR^{10}$, $S(O)_qR^{10}$ where q is 0, 1 or 2, $CONR^7R^8$, CN or $S(O)_qNR^7R^8$; two $R^4$ substituents may be attached to the same carbon atom to form $C(R^4)_2$, where each $R^4$ is the same or different, or $C(R^4)_2$ may represent C=O;

$R^5$ is alkyl, cycloalkyl, aryl, heteroaryl, heterocyclo, $CF_3$, $OR^9$, $COR^{10}$, $S(O)_qR^{10}$, $CO_2R^{14}$, $CONR^7R^8$, $S(O)_q NR^7R^8$, halogen, $NR^{10}R^{11}$ or CN, or two adjacent $R^5$ substituents may be combined to form a heterocyclic ring;

$R^6$ is $OR^9$, $COR^{10}$, $CO_2R^{15}$, $CONR^7R^8$, $NR^{10}R^{11}$, $S(O)_q R^{10}$, $S(O)_q NR^7R^8$ =O, =NOR$^{10}$, succinimido or the group

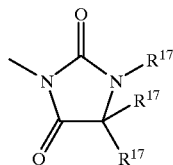

$R^7$ and $R^8$, which may be the same or different, are each H, alkyl, cycloalkyl, aryl, heteroaryl, heterocyclo, arylalkyl, heteroarylalkyl, heterocycloalkyl or cycloalkylalkyl, or $R^7$ and $R^8$ and the nitrogen to which they are attached together represent a heterocyclic ring;

$R^9$ is H, alkyl, $CF_3$, $CHF_2$, $CH_2F$, cycloalkyl, aryl, heteroaryl, heterocyclo, arylalkyl, heteroarylalkyl, heterocycloalkyl or cycloalkylalkyl;

$R^{10}$ is H, alkyl, cycloalkyl, aryl, heteroaryl, heterocyclo, arylalkyl, heteroarylalkyl, heterocycloalkyl or cycloalkylalkyl; and $R^{11}$ is H, alkyl, cycloalkyl, aryl, heteroaryl, heterocyclo, arylalkyl, heteroarylalkyl, heterocycloalkyl, cycloalkylalkyl, $COR^{12}$, $CONR^7R^8$, $S(O)_qR^{12}$ or $S(O)_qNR^7R^8$;

or $R^{10}$ and $R^{11}$ and the nitrogen to which they are attached together represent a heterocyclic ring;

$R^{12}$ is $OR^9$ or $R^{13}$;

$R^{13}$ is alkyl, cycloalkyl, aryl, heteroaryl, heterocyclo, arylalkyl, hetarylalkyl, heterocycloalkyl or cycloalkylalkyl;

$R^{14}$ is H, alkyl or cycloalkyl;

$R^{15}$ is H, alkyl, cycloalkyl, arylalkyl or heteroarylalkyl;

X is a bond (i.e. is absent), —O—, —C(O)—, —S(O)$_q$—, —N(R$^{11}$)—, —N(R$^{11}$)C(R$^{16}$)$_2$—, —S(O)$_q$C(R$^{16}$)$_2$—, —C(R$^{16}$)$_2$N(R$^{11}$)—, —C(R$^{16}$)$_2$S(O)$_q$—, —C(R$^{16}$)=N—, —N=C(R$^{16}$)—, —N(R$^{11}$)SO$_2$—, —SO$_2$N(R$^{11}$)—, —N(R$^{11}$)CO— or —CON(R$^{11}$)—; and the $R^{16}$ groups in C(R$^{16}$)$_2$ may be the same or different;

Y is a bond (i.e. is absent), —O—, —C(O)—, S(O)$_q$—, —N(R$^{11}$)—, —N(R$^{11}$)C(R$^{16}$)$_2$—, —S(O)$_q$C(R$^{16}$)$_2$—, —C(R$^{16}$)$_2$N(R$^{11}$)—, —C(R$^{16}$)$_2$S(O)$_q$—, —C(R$^{16}$)=N—, —N=C(R$^{16}$)—, —N(R$^{11}$)SO$_2$—, —SO$_2$N(R$^{11}$)—, —N(R$^{11}$)CO— or —CON(R$^{11}$)—; and the $R^{16}$ groups in C(R$^{16}$)$_2$ may be the same or different;

$R^{16}$ is H, alkyl, cycloalkyl, $OR^9$, $CO_2R^{14}$, $COR^{10}$, $S(O)_q R^{10}$, $CONR^7R^8$, CN or $S(O)_q NR^7R^8$;

$R^{17}$ is H or alkyl;

W is alkyl, cycloalkyl, cycloalkylalkyl, aryl, arylalkyl, heteroaryl, heteroarylalkyl, heterocyclo or heterocycloalkyl;

represents a single or double bond;

each k and m is independently 0, 1, 2 or 3;

n is 0, 1 or 2; and p is 0, 1 or 2, provided that n+p does not exceed 3;

or a salt, solvate, hydrate, N-oxide, protected amino, protected carboxy or protected hydroxamic acid derivative thereof

DESCRIPTION OF THE INVENTION

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

It will further be appreciated that the compounds according to the invention may contain an oxime. This oxime can give rise to geometrical isomers, and in each case the invention is to be understood to extend to all such isomers and mixtures thereof.

As used in this specification, alone or in combination, the term "alkyl" refers to straight or branched chain alkyl moiety having from one to six carbon atoms, including for example, methyl, ethyl, propyl, isopropyl, butyl, tert-butyl, pentyl, hexyl and the like.

The term "alkenyl" refers to a straight or branched chain alkyl moiety having two to six carbon atoms and having in addition one double bond, of either E or Z stereochemistry where applicable. The term alkenyl includes for example, vinyl, 1-propenyl, 1- and 2-butenyl, 2-methyl-2-propenyl and the like.

The term "alkynyl" refers to a straight or branched chain alkyl moiety having two to six carbon atoms and having in addition one triple bond. The term alkynyl includes for example, ethynyl, 1-propynyl, 1- and 2-butynyl, 1-methyl-2-butynyl and the like.

Cycloalkyl or carbocyclic ring refers to a non-aromatic cyclic or multicyclic, saturated or partially saturated ring system having from three to ten carbon atoms which may be optionally benzofused at any available position. Thus cycloalkyl includes, for example, cyclopropyl, cyclobutyl, cyclopentyl, cyclohexyl, cycloheptyl, cyclooctyl, tetrahydronaphthyl, bicyclo[2.2.1]heptanyl, bicyclo[2.2.1] heptenyl, cyclopentenyl, indanyl and the like.

Heterocyclo or heterocyclic ring refers to a 3 to 10 membered saturated or partially saturated monocyclic or saturated or partially saturated multicyclic hydrocarbon ring system in which one or more of the atoms in the ring system is an element other than carbon, chosen from amongst nitrogen, oxygen or sulphur (or oxidised versions thereof, such as N-oxide, sulphoxide, sulphone). Examples include azetidinyl, pyrrolidinyl, tetrahydrofuryl, piperidinyl, quinuclidinyl, tetrahydropyranyl, morpholinyl, thiomorpholinyl, piperazinyl, N-alkyl-piperazinyl, homopiperazinyl, oxazolidinyl, imidazolidinyl, thiazolidinyl, pyrazolidinyl, benzodioxole, [2,3-dihydro] benzofuryl, [3,4-dihydro]benzopyranyl, 1,2,3,4 tetrahydroquinolinyl, 1,2,3,4 tetrahydroisoquinolinyl, 8-oxabicyclo[3.2.1]octane, indolinyl, isoindolinyl, and the like.

Aryl indicates carbocyclic radicals containing 6 to 10 carbon atoms and containing either a single ring or two condensed rings. Thus aryl includes, for example, phenyl and naphthyl.

Heteroaryl refers to a 5 to 10 membered aromatic monocyclic or multicyclic hydrocarbon ring system in which one or more of the atoms in the ring system is an element other than carbon, chosen from amongst nitrogen, oxygen or sulphur (or oxidised versions thereof, such as N-oxide). In general, the heteroaryl groups may be for example monocyclic or bicyclic fused ring heteroaryl groups. Monocyclic heteroaryl groups include, for example, five- or six-membered heteroaryl groups containing one, two, three or four heteroatoms selected from oxygen, sulphur or nitrogen atoms. Bicyclic heteroaryl groups include for example eight- to ten-membered fused-ring heteroaryl groups containing one, two or more heteroatoms selected from oxygen, sulphur or nitrogen atoms.

The term heteroaryl includes, for example, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, pyridyl, pyrimidinyl, pyridazinyl, pyrazinyl, 1,3,5-triazinyl, 1,2,4-triazinyl, 1,2,3-triazinyl, benzofuryl, benzothienyl, benzotriazolyl, indolyl, isoindolyl, benzimidazolyl, imidazo[1,2-a]pyridyl, benzothiazolyl, benzoxazolyl, benzisoxazolyl, benzopyranyl, quinazolinyl, quinoxalinyl, naphthyridinyl, pyrido[3,4-b]pyridyl, pyrido[3,2-b]pyridyl, pyrido[4,3-b]-pyridyl, quinolinyl, isoquinolinyl, phthalazinyl, tetrazolyl and the like.

Arylalkyl includes an aryl-alkyl- group wherein the aryl and alkyl are as described herein. Heteroarylalkyl includes a heteroaryl-alkyl-group, cycloalkylalkyl includes a cycloalkyl-alkyl-group and heterocycloalkyl includes a heterocyclo-alkyl-group, wherein all groups are as defined above.

The term "halogen" includes fluorine, chlorine, bromine or iodine.

The term "benzofused" means the addition of a benzene ring sharing a common bond with the defined ring system.

The term "optionally substituted" means optionally substituted by one or more of the groups specified, at any available position or positions.

The terms "protected amino", "protected carboxy" and "protected hydroxamic acid" mean amino, carboxy and hydroxamic acid groups which can be protected in a manner familiar to those skilled in the art. For example; an amino group can be protected by a benzyloxycarbonyl, tert-butoxycarbonyl, 2,2,2-trichloroethoxycarbonyl, acetyl or like group, or may be in the form of a phthalimido or like group. A carboxyl group can be protected in the form of a readily-cleavable ester such as the methyl, ethyl, benzyl or tert-butyl ester. A hydroxamic acid may be protected as either N or O-substituted derivatives, such as O-benzyl or O-tert-butyldimethylsilyl.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R$ where R may be an ethyl, benzyl, phenethyl, phenylpropyl, α or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Preferred compounds of the invention are those wherein any one or more of the following may apply:

One group of compounds of the invention has the formula (I) in which $R^1$ is NHOH.

In one preferred group of compounds of formula (I) $R^2$ is in particular isopropyl or isobutyl, especially isopropyl.

Another preferred group of compounds of formula (I) is where $R^2$ is a substituted alkyl group, especially substituted methyl, ethyl or propyl. $R^2$ in compounds of this type is preferably substituted by $R^6$, where $R^6$ is especially $CO_2R^{15}$, in particular $CO_2H$, $CONR^7R^8$, $NR^{10}R^{11}$, succinimido or the group

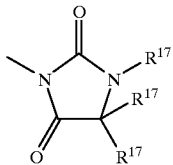

In compounds of this type $CONR^7R^8$ is in particular $CONH_2$, CON(H)alkyl, $CON(alkyl)_2$ or $R^7$ and $R^8$ are attached together to form a heterocyclic ring. $NR^{10}R^{11}$ in compounds of this type is especially $N(H)COR^{12}$ or $N(alkyl)COR^{12}$, particularly preferred is where $R^{12}$ is alkyl. Each $R^{17}$ in compounds of the invention is in particular methyl.

A further preferred group of compounds of the invention has the formula (I) where $R^2$ is an optionally substituted cycloalkyl or heterocyclo group, especially an optionally substituted heterocyclo group. In compounds of this type $R^2$ is in particular azetidinyl, pyrrolidinyl, piperidinyl, piperazinyl, tetrahydrofuryl or tetrahydropyranyl, especially optionally substituted piperidinyl. When substituted compounds of this type may in particular be substituted by $R^6$, especially where $R^6$ is $CO_2R^{15}$. $R^{15}$ may in particular be arylalkyl or heteroarylalkyl, preferably arylalkyl, especially benzyl.

$R^3$ in compounds of the invention may in particular be a hydrogen atom.

One group of compounds of the invention has the formula (I) in which $R^2$, $R^3$ and the carbon atom to which they are attached together represent an optionally substituted carbocylic or heterocyclic ring. Especially preferred compounds in this group are those where $CR^2R^3$ is a cycloalkyl or a heterocyclic ring, in particular, $C_{3-7}$ cycloalkyl groups, especially, cyclopropyl, cyclobutyl, cyclopentyl and cyclohexyl groups, and $C_{3-7}$ heterocyclo groups, especially, azetidinyl, pyrrolidinyl, tetrahydrofuryl, tetrahydropyranyl, piperidinyl and piperazinyl. In compounds of this type $CR^2R^3$ is in particular cyclobutyl, cyclopentyl, cyclohexyl or tetrahydropyranyl, especially tetrahydropyranyl.

In another group of compounds of the invention Y is preferably a bond. In compounds of this type X is in particular $N(R^{11})$, O or $S(O)_q$. Particularly preferred is where X is NH, O or S.

In compounds of the invention k is preferably 0.

When present, $R^5$ in compounds of formula (I) is preferably $CF_3$, $OR^9$, CN, F, Cl, Br, I or $CON^7R^8$. $R^5$ is in particular $CF_3$, $OCH_3$, $OCF_3$, $OCHF_2$, $OCH_2F$, $CONH_2$, $CONHCH_3$, $CON(CH_3)_2$, CN, F, Cl, Br or I. In compounds where $R^5$ is present m is preferably 1, 2, . . . especially 1.

----- is preferably a double bond.

An especially preferred group of compounds has the general formula (Ia)

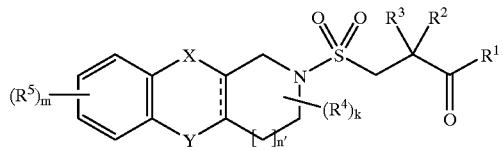

(Ia)

wherein $R^1$, $R^2$, $R^3$, $R^4$, $R^5$, X, Y, k and m are as previously described and n' is 0 or 1. In compounds of this type, n' is preferably 1. Particularly preferred compounds of the invention are:

N-Hydroxy-3-methyl-2-(1,3,4,9-tetrahydro-β-carboline-2-sulfonylmethyl)-butyramide;

2-(3,4-Dihydro-1H-benzo[4,5]furo[2,3-c]pyridine-2-sulfonylmethyl)-N-hydroxy-3-methylbutyramide;

N-Hydroxy-2-(6-methoxy-1,3,4,9-tetrahydro-β-carboline-2-sulfonylmethyl)-3-methylbutyramide;

(1,3,4,9-Tetrahydro-β-carboline-2-sulfonylmethyl)-tetrahydro-pyran-4-carboxylic acid hydroxamide;

(R)-2-(3,4-Dihydro-1H-benzo[4,5]thieno[2,3-c]pyridine-2-sulfonylmethyl)-N-hydroxy-3-methyl-butyramide;

4-(3,4-Dihydro-1H-benzo[4,5]thieno[2,3-c]pyridine-2-sulfonylmethyl)-tetrahydro-pyran-4-carboxylic acid hydroxamide;

4-[1-Hydroxycarbamoyl-2-(1,3,4,9-tetrahydro-β-carboline-2-sulfonyl)-ethyl]-piperidine-1-carboxylic acid benzyl ester;

and the salts, solvates, hydrates, N-oxides, protected amino, protected carboxy and protected hydroxamnic acid derivatives thereof.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below, the various groups R and other variables are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience (1999).

Thus, for example, compounds of the invention may be prepared by the following general route:

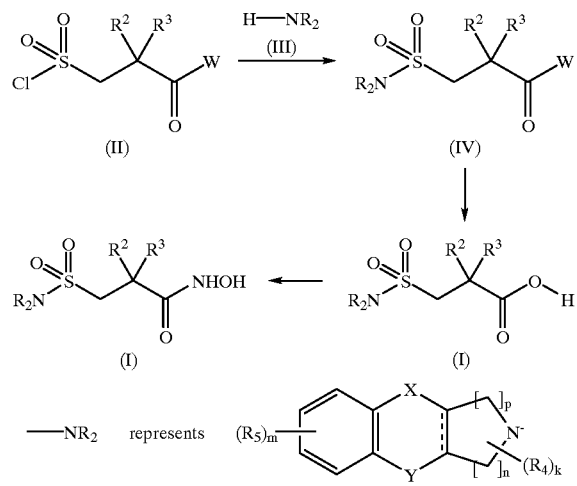

Compounds of formula (IV), where W is for example an alkoxy group, such as methoxy, ethoxy or tert-butoxy or a chiral auxiliary, for example, 4-(R)-benzyl-oxazolidin-2-one maybe prepared by methods well known in the literature, for example, by reaction of a sulfonyl chloride (II) with an amine (III) in the presence of an amine base, such as triethylamine in a halogenated solvent, such as dichloromethane at room temperature.

Compounds of general formula (II) are either known or may be made by one skilled in the art using conditions known in the literature, see for example WO-A-99/24399, or as described in the examples herein after. Compounds of general formula (III) are available commercially or they be made using methods known in the literature or by any method known to those skilled in the art.

Carboxylic acids of general formula (I) may be prepared by deprotection of a suitably protected carboxylic acid of formula (IV). For example, where W is an alkoxy group, such as ethoxy, a base such as aqueous lithium hydroxide may be used, alternatively trifluoroacetic acid may be used when W is a tert-butyl group or in the case of a chiral auxiliary such as 4-(R)-benzyl-oxazolidin-2-one, lithium hydroxide/hydrogen peroxide may be used. Appropriate solvent and temperature conditions such as those described in the examples herein after may be used.

Compounds of formula (I) may also be prepared by interconversion of other compounds of formula (I). Thus, for example, hydroxamic acids of general formula (I) may be prepared using conditions well known in the literature. For example, treatment of acids of formula (I) with oxalyl chloride in an inert solvent (such as dichloromethane) gives an intermediate acid chloride, which may or may not be isolated, but which in turn is reacted with hydroxylamine at a suitable temperature such as room temperature to give the desired hydroxamic acids (I). Alternatively an acid of formula (I) maybe activated in situ using for example a diimide such as 1-(3-dimethylaminopropyl)-3-ethylcarbodiimide hydrochloride, advantageously in the presence of a catalyst such as a N-hydroxy compound, e.g. N-hydroxybenzotriazole using suitable conditions, e.g. in N,N dimethylformamide at −15° C., prior to the subsequent addition of a suitably protected hydroxylamine such as tert-butyldimethyl silyl hydroxylamine and warming to ambient temperature. The protecting group maybe removed using appropriate conditions, such as water or tetrabutylammonium fluoride and acetic acid in tetrahydrofuran at 0° C., to yield the desired hydroxamic acids of formula (I). Similarly a compound of formula (I) where X or Y is a N atom suitably protected by, for example, a 2,2,2-trichloroethyl ester group may be deprotected, using for example, sodium hydroxide in methanol to give a compound of formula (I) where X or Y is NH.

Similarly, intermediates of any appropriate formula may be prepared by the interconversion of other compounds of the same formula.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysin, collagenase, gelatinase, ADAM or ADAM-TS enzymes. Compounds according to the invention may also exhibit in vitro inhibition of membrane-shedding events known to be mediated by metalloproteinases, for example, α-APP, ACE, TGF-α, TNF-α, Fas ligand, selecting, TNFR-I, TNFR-II, CD30, Il-6R, CD43, CD44, CD16-I, CD16-II, Folate receptor, CD23, or IL-1RII.

The activity and selectivity of the compounds may be determined by use of the appropriate enzyme inhibition test, for example as described in Examples A-M of WO-A-98/05635, by the assay for the inhibition of CD23 shedding described in WO-A-99/24399, or by the assay of TNF RI shedding described in WO-A-00/56704.

This invention also relates to a method of treatment for patients (including man and/or mammalian animals raised in the dairy, meat or fur industries or as pets) suffering from disorders or diseases which can be attributed to metalloproteinases.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF, MMPs, ADAM or ADAM-TS enzymes. Accordingly in another aspect, this invention concerns:

a method of management (by which is meant treatment or prophylaxis) of disease or conditions mediated by TNF, MPs, ADAM or ADAM-TS enzymes in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNF, MMPs, ADAM or ADAM-TS enzymes; and the use of a compound of formula (I) in the preparation of an agent for the management (by which is meant treatment or prophylaxis) of diseases or conditions mediated by TNF, MMPs, ADAM or ADAM-TS enzymes.

The disease or conditions referred to above include inflammatory diseases, autoimmune diseases, cancer, cardiovascular diseases and diseases involving tissue breakdown. Appropriate diseases include rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, bacterial infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis, aspirin-independent anti-thrombosis, systemic lupus erythematosus and solid organ transplant.

Compounds of formula (I) may also be useful in the treatment of pelvic inflammatory disease (PID), age-related macular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD).

Compounds of the invention are particularly of use in the treatment of inflammatory diseases, autoimmune diseases and cancer. Thus, for example, the compounds may be used in the treatment (including prophylaxis) of graft versus host reactions, psoriasis, atopic dermatitis, rhinitis, eczema, systemic lupus erythematosus, solid organ transplant, cystic fibrosis, rheumatoid arthritis, osteoarthritis, osteoporosis, Crohn's Disease, ulcerative colitis, multiple sclerosis, periodontitis, bone resorption, bacterial infections, epidermolysis bullosa, tumour growth, angiogenesis, ophthalmological disease, retinopathy, asthma, emphysema, bronchitis, and chronic obstructive pulmonary disease (COPD).

For the treatment of all diseases and disorders previously indicated, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques.

Ocular injection, such as intravitreal, subtenons, subconjunctival, periocular and retrobulbar may also be used, as well as intraocular slow release devices and implants. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. No. 4,256,108, U.S. Pat. No. 4,166,452 and U.S. Pat. No. 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc, containing a compound of the invention are employed. For the purposes of this specification, topical application includes mouthwashes and gargles.

For topical ocular administration, pharmaceutically acceptable solutions, suspensions or gels containing a compound of formula (I) may be used. Solutions and suspensions may also be adapted for intra-vitreal or intra-cameral use.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention.
In the Examples the following abbreviations are used:
h=hour TLC-thin layer chromatography

INTERMEDIATE 1

1,3,4,9-Tetrahydro-β-carboline-2-carboxylic Acid tert-Butyl Ester 1,2,3,4-Tetrahydro-9H-pyrido[3,4-b]indole (5.0 g), di-tert-butyldicarbonate (6.3g) and triethylamine (4.0 ml) in dichloromethane (100 ml) were stirred under nitrogen at room temperature for 30 minutes. The mixture was poured into brine (100 ml) and extracted with dichloromethane (100 ml). The organic layer was washed with water (150 ml) then dried ($MgSO_4$) and the solvent removed under reduced pressure to give the title compound (7.68 g, 97%) as an off white solid.

$R_f$ 0.54 (5% methanol in dichloromethane)

INTERMEDIATE 2

3,4-Dihydro-1H-β-carboline-2,9-dicarboxylic Acid 2-tert-Butyl Ester 9-(2,2,2-Trichloro-ethyl)Ester 1,3,4,9-Tetrahydro-β-carboline-2-carboxylic acid tert-butyl ester (7.68 g), 2,2,2-trichloroethylchloroformate (5.8 ml), sodium hydroxide (2.8 g) and tetrabutylammonium iodide (catalytic) in dichloromethane (100 ml) were stirred under nitrogen at room temperature for 5 h. The mixture was diluted with dichloromethane (100 ml), washed with water (150 ml) and brine (100 ml), then dried ($MgSO_4$) and the solvent removed under reduced pressure. The residue was chromatographed ($SiO_2$, 1% methanol in dichloromethane) to give the title compound (3.53 g, 28%) as a yellow foam.

$R_f$ 0.60 (2.5% methanol in dichloromethane).

INTERMEDIATE 3

1,2,3,4-Tetrahydro-β-carboline-9-carboxylic Acid 2,2,2-Trichloro-ethyl Ester 3,4-Dihydro-1H-β-carboline-2,9-dicarboxylic acid 2-tert-butyl ester 9-(2,2,2-trichloro-ethyl) ester (3.53 g) and trifluoroacetic acid (5 ml) in dichloromethane (30 ml) were stirred at room temperature for 1.5 h. The mixture was partitioned between 6N NaOH solution (70 ml) and dichloromethane (50 ml). The dichloromethane was washed with water (50 ml) and dried ($MgSO_4$) then the solvent removed under reduced pressure to give the title compound (2.25 g, 81%) as a yellow solid.

$R_f$ 0.30 (10% methanol in dichloromethane).

INTERMEDIATE 4

4-Benzenesulfonyloxy-piperidine-1-carboxylic Acid Benzyl Ester

Triethylamine (17 ml) was added dropwise to a solution of benzyl 4-hydroxy-1-piperidinecarboxylate (28.83 g) in dichloromethane (100 ml) at 0° C. and stirred for 15 minutes. Benzenesulfonyl chloride (14 ml) was added and the reaction allowed to stir at room temperature for 48 h. The mixture was washed with water (50 ml), saturated sodium bicarbonate solution (50 ml), water (50 ml) and brine (50 ml) then dried ($Na_2SO_4$), filtered and evaporated under reduced pressure. The residue was purified by chromatog raphy (SiO$_2$, 20% ethyl acetate in hexane to 30% ethyl acetate in hexane) to give the title compound (31.88 g, 77%) as a white crystalline solid.

R$_f$ 0.62 (5% methanol in dichloromethane).

INTERMEDIATE 5

2-(1-Benzyloxycarbonyl-piperidin-4yl)-malonic Acid

Sodium metal (3.2 g) was dissolved in ethanol (50 ml) under a nitrogen atmosphere at room temperature. A solution of diethyl malonate (56.4 ml) in ethanol (50 ml) was added dropwise, followed by a solution of 4-benzenesulfonyloxy-piperidine-1-carboxylic acid benzyl ester (31.88 g) in ethanol (50 ml), also added dropwise. The mixture was heated to reflux for 16 h then the solvent was removed under reduced pressure. The residue was partitioned between water (100 ml) and diethyl ether (100 ml) and the aqueous washed with further diethyl ether (60 ml). The combined organics were washed with 10% citric acid solution (50 ml), water (50 ml) and brine (50 ml). After drying (Na$_2$SO$_4$) and filtering the solvent was removed under reduced pressure to leave a yellow liquid. Half of this crude diester was taken and dissolved in methanol (150 ml) and water (50 ml). Lithium hydroxidemonohydrate (18.14 g) was added slowly and the reaction left to stir at room temperature for 16 h then the methanol was removed under reduced pressure. The aqueous was washed with diethyl ether (3×40 ml), acidified to pH=3 with citric acid and extracted with ethyl acetate (2×40 ml). The combined organics were washed with water (2×40 ml) and brine (40 ml), dried (Na$_2$SO$_4$), filtered and evaporated under reduced pressure to give the title compound (8.29 g, 56%) as a white crystalline solid.

R$_f$ 0.47 (5% methanol in dichloromethane).

INTERMEDIATE 6

4-(1-Carboxy-vinyl)-piperidine-1carboxylic Acid Benzyl Ester 2-(1-Benzyloxycarbonyl-piperidin-4-yl)-malonic acid (18.06 g) was dissolved in tetrahydrofuran (140 ml) and morpholine (4.95 ml) followed by acetic acid (6.43 ml) was added, forming a white precipitate. Formaldehyde (4.56 g) was added, causing the precipitate to disappear, and the mixture heated to reflux for 4 h. The solvent was evaporated, diethyl ether (50 ml) added and the mixture extracted with water (3×60 ml). The aqueous was acidified to pH=3 with citric acid and extracted with diethyl ether (3×30 ml). The combined organic extracts were washed with water (40 ml) and brine (40 ml), dried (Na$_2$SO$_4$), filtered and the solvent removed under reduced pressure to give the title compound (16.65 g) as a mixture containing approximately 10% of the acid starting material.

R$_f$ 0.5 (5% methanol in dichloromethane).

INTERMEDIATE 7

4-(2-Acetylsulfanyl-1-carboxy-ethyl)-piperidine-1-carboxylic Acid Benzyl Ester 4-(1-Carboxy-vinyl)-piperidine-1-carboxylic acid benzyl ester (15.6 g) was dissolved in thioacetic acid (15 ml) and heated to reflux for 3 h. The thioacetic acid was evaporated under reduced pressure and azeotroped with 1:1 hexane-dichloromethane (4×30 ml) to give the title compound (20.32 g, 95%) as an orange oil.

R$_f$ 0.28 (40% ethyl acetate in hexane).

INTERMEDIATE 8

4-(2-Acetylsulfanyl-1-tert-butoxycarbonyl-ethyl)-piperidine-1-carboxylic Acid Benzyl Ester Sulfuric acid (1.15 ml) was added slowly to a solution of 4-(2-acetylsulfanyl-1-carboxy-ethyl)-piperidine-1-carboxylic acid benzyl ester (20.32 g) in dichloromethane (60 ml). The mixture was cooled in an acetone/dry ice bath and cooled isobutylene (60 ml) added. The mixture was transferred to a Parr high pressure apparatus and left to stir overnight then washed with water (30 ml), saturated sodium bicarbonate solution (30 ml) and brine (30 ml). After drying (Na$_2$SO$_4$) and filtering the solvent was removed under reduced pressure and the residue purified by column chromatography (SiO$_2$, 20% ethyl acetate in hexane) to give the title compound (11.22 g, 60%) as an orange oil.

R$_f$ 0.25 (20% ethyl acetate in hexane).

INTERMEDIATE 9

4-(1-tert-Butoxycarbonyl-2-chlorosulfonyl-ethyl)-piperidine-1-carboxylic Acid Benzyl Ester A solution of 4-(2-acetylsulfanyl-1-tert-butoxycarbonyl-ethyl)-piperidine-1-carboxylic acid benzyl ester (1.01 g) in dichloromethane (25 ml) and water (25 ml) was cooled in ice. Chlorine gas (500 mg) was bubbled through the solution over 10 minutes then the mixture was flushed with nitrogen gas. The mixture was washed with water (25 ml) and brine (25 ml), then. dried (Na$_2$SO$_4$), filtered and the solvent removed under reduced pressure to give the title compound (920 mg, 86%) as a colourless oil.

R$_f$ 0.48 (30% ethyl acetate in hexane).

INTERMEDIATE 10

4-Iodomethyl-tetrahydro-pyran-4-carboxylic Acid Methyl Ester

Lithium diisopropylamide (10.9 ml of 2.0M solution in heptane/tetrahydrofuran/ethylbenzene) was added to a stirred solution of tetrahydro-pyran-4-carboxylic acid methyl ester (3.00 g) in tetrahydrofuran (50 ml) at 0° C. under an atmosphere of nitrogen. The mixture was stirred for 30 minutes before dropwise addition of diiodomethane (2.51 ml). Stirring was continued for a further hour during which it warmed to room temperature. The reaction was poured into water (50 ml) and then extracted with diethyl ether (3×40 ml). The combined organics were washed with water (2×20 ml), 2M hydrochloric acid (20 ml), water (20 ml) and brine (20 ml). After drying (MgSO$_4$), filtering and evaporating under reduced pressure a yellow oil was obtained which was purified by column chromatography eluting with 3:1 hexane/diethyl ether to give the title compound as a colourless oil (3.11 g, 53%).

R$_f$ 0.26 (3:1 hexane/diethyl ether).

INTERMEDIATE 11

4-Acetylsulfanylmethyl-tetrahydro-pyran-4-carboxylic Acid Methyl Ester

4-Iodomethyl-tetrahydro-pyran-4-carboxylic acid methyl ester (3.05 g) was dissolved in N,N-dimethylformamide (20 ml) at room temperature and potassium thioacetate (1.47 g) added. The mixture was stirred for 18 hours then diluted with water (50 ml) and extracted with diethyl ether (4×25 ml). The combined organics were washed with saturated sodium bicarbonate solution (3×20 ml) and brine (20 ml), then dried (MgSO$_4$), filtered and evaporated under reduced pressure to give the title compound as a yellow solid (2.42 g, 97%).

R$_f$ 0.44 (1:1 hexane/diethyl ether).

INTERMEDIATE 12

4-Chlorosulfonylmethyl-terahydro-pyran-4-carboxylic Acid Methyl Ester

A suspension of 4-acetylsulfanylmethyl-tetrahydro-pyran-4-carboxylic acid methyl ester (4.6 g) in aqueous acetic acid (5 ml in 100 ml water) was stirred with cooling in an ice bath. Chlorine was bubbled through for 20 minutes then dichloromethane (50 ml) added to dissolve the suspension and the bubbling through of chlorine gas continued for a further 15 minutes. The mixture was separated and the aqueous layer extracted with dichloromethane (30 ml). The combined organics were washed with ice cold water (2×50 ml) and brine (40 ml), dried (MgSO$_4$) filtered and evaporated under reduced pressure to give the title compound as a white crystalline solid (4.9 g, 95%).

R$_f$ 0.63 (diethyl ether).

INTERMEDIATE 13

4(R)-Benzyl-3-(3-methylbutyryl)oxazolidin-2-one

N-Butyllithium (2M in hexanes, 50 ml) was added to a solution of 4-(R)-benzyloxazolidin-2-one (17 g) in tetrahydrofuran at −78° C. and the suspension was stirred for 30 minutes, then isovaleryl chloride (12 g) was added dropwise. The solution was stirred for 30 min, allowed to warm to room temperature, and saturated ammonium chloride (200 ml) was added. The mixture was evaporated in vacuo and extracted with diethyl ether (2×100 ml), the solvent washed with water and saturated brine, dried (Na$_2$SO$_4$) and evaporated to give the title compound as a colourless solid (25.0 g, 95%

TLC R$_f$ 0.54 (1:1 diethyl ether/hexane).

INTERMEDIATE 14

4-(R)-Benzyl-3-(2-(R)-hydroxymethyl-3-methylbutyryl) oxazolidin-2-one

Titanium tetrachloride (18 ml) was added dropwise to a solution of 4-(R)-benzyl-3-(3-methylbutanoyl)oxazolidin-2-one (41.5 g) in dichloromethane (300 ml) at 0° C. Diisopropylethylamine (28 ml) was added dropwise and the resulting purple suspension was stirred for 30 min, then a solution of trioxane (11.2 g) was added, followed by titanium tetrachloride (18 ml) and the mixture was stirred for two hours, during which time the solution changed in colour from purple to amber. Ammonium chloride (400 ml saturated aqueous solution) was added and the mixture was stirred for 10 min, then the phases separated and the organic layer washed with water and saturated brine, dried (Na$_2$SO$_4$) and evaporated to give the title compound as a colourless solid (45 g).

TLC R$_f$ 0.34 (1:1 diethyl ether/hexane).

INTERMEDIATE 15

4-(R)-Benzyl-3-(2-iodomethyl-3-methylbutyryl) oxazolidin-2-one

Iodine (42 g), triphenylphosphine (47 g) and imidazole (12 g) were added to a solution of 4-(R)-benzyl-3-(2-(R)-hydroxymethyl-3-methylbutanoyl)oxazolidin-2-one (45 g) in toluene (400 ml) and the mixture was heated to 80° C. for 1 h, then cooled and washed with water and saturated brine. The solvent was dried (Na$_2$SO$_4$) and evaporated and the residue filtered through silica (200 g) eluting with diethyl ether-hexane 1:1 to give the title compound as a yellow viscous oil (56.4 g).

TLC R$_f$ 0.60 (1:1 hexane-diethyl ether).

INTERMEDIATE 16

4-(R)-Benzyl-3-(2-(R)-acetylthiomethyl-3-methylbutyryl)oxazolidin-2-one

Potassium thioacetate (19 g) was added to a solution of the 4-(R)-benzyl-3-(2-iodomethyl-3-methylbutanoyl) oxazolidin-2-one (56 g) in N,N-dimethylformamide (200 ml), and the mixture was stirred for 3 h at room temperature, then poured into water (600 ml). The mixture was extracted with diethyl ether (2×500 ml) and the organic solvent washed with water and saturated brine, dried (Na$_2$SO$_4$) and evaporated to give the title compound as a pale amber oil (48.6 g).

TLC R$_f$ 0.43 (1:1 diethyl ether/hexane).

INTERMEDIATE 17

4-(R)-Benzyl-3-(2-(R)-chlorosulfonylmethyl-3-methylbutyryl)oxazolidin-2-one

A solution of 4-(R)-benzyl-3-(2-(R)-acetylthiomethyl-3-methylbutyryl) oxazolidin-2-one (42.5 g) in dichloromethane (500 ml) and water (400 ml) was cooled in ice and chlorine bubbled through the suspension, while stirring vigorously, for 1 h, following the progress of the reaction by TLC. On complete conversion of the starting material to the desired product, the reaction mixture was flushed with nitrogen for 10 min, then the phases separated. The organic layer was washed with cold water (2×300 ml) and saturated brine, dried (Na$_2$SO$_4$) and evaporated to give the title compound as a pale yellow viscous oil (42 g).

TLC R$_f$ 0.37 (1:1 diethyl ether/hexane).

INTERMEDIATE 18

2-(6-Methoxy-1,3,4,9-tetrahydro-β-carboline-2-sulfonylmethyl)-3-methylbutyric Acid tert-Butyl Ester A solution of 2-chlorosulfonylmethyl-3-methylbutyric acid tert-butyl ester (WO 99/24399) (470mg) in dichloromethane (10 ml) was added to a mixture of 6-methoxy-1,2,3,4-tetrahydro-9H-pyrido[3,4-b]indole (350 mg) and triethylamine (0.72 ml) in dichloromethane (10 ml) at room temperature under nitrogen. The mixture was stirred for 20 minutes before being evaporated to dryness and the residue chromatographed (SiO$_2$, 1:1 heptane-ethyl acetate) to give the title compound (487 mg, 66%) as a white solid.

R$_f$ 0.59 (1:1 heptane-ethyl acetate).

The following compounds were prepared in a similar manner:

INTERMEDIATE 19

2-(3,4-Dihydro-1H-benzo[4,5]furo[2,3-c]pyridine-2-sulfonylmethyl)-3-methylbutyric Acid tert-Butyl Ester From 1,2,3,4-tetrahydrobenzo[4,5]furo[2,3-c]pyridine (350 mg) to give, after chromatography (SiO$_2$, 2:1 heptane-ethyl acetate), the title compound (610 mg, 69%) as a white solid.

R$_f$ 0.78 (1:1 heptane-ethyl acetate).

INTERMEDIATE 20

2-(4-Methoxycarbonyl-tetrahydro-pyran-4-ylmethane sulfonyl)-1,2,3,4-tetrahydro-β-carboline-9-carboxylic Acid 2,2,2-Trichloro-ethyl Ester From 4-chlorosulfonylmethyl-tetrahydro-pyran-4-carboxylic acid methyl ester (0.32 g) and 1,2,3,4-tetrahydro-β-carboline-9-carboxylic acid 2,2,2-trichloro-ethyl ester (0.50 g) to give, after chromatography (SiO$_2$, 33% ethyl acetate in heptane then 50% ethyl acetate in heptane), the title compound (556 mg, 69%) as a white solid.

R$_f$ 0.30 (50% ethyl acetate in heptane).

INTERMEDIATE 21

2-[2-(1-Benzyloxycarbonyl-piperidin-4-yl)-2-tert-butoxy carbonyl-ethanesulfonyl]-1,2,3,4-tetrahydro-β-carboline-9-carboxylic Acid 2,2,2-Trichloro-ethyl Ester Prepared from 4-(1-tert-butoxycarbonyl-2-chlorosulfonyl-ethyl)-piperidine-1-carboxylic acid benzyl ester (640 mg) and 3,4-dihydro-1H-β-carboline-2,9-dicarboxylic acid 2-tert-butyl ester 9-(2,2,2-trichloro-ethyl) ester (500 mg) to give, after chromatography (SiO$_2$, 2:1 heptane-ethyl acetate), the title compound (608 mg, 61%) as a white solid.

R$_f$ 0.26 (2: 1 heptane-ethyl acetate).

INTERMEDIATE 22

4(R)-Benzyl-3-[2-(R)-(3,4dihydro-1H-benzo[4,5]thieno[2,3-c]pyridine-2-sulfonylmethyl)-3-methyl-butanoyl]-oxazolidin-2-one 4-(R)-Benzyl-3-(2-(R)-chlorosulfonylmethyl-3-methylbutyryl)oxazolidin-2-one (370 mg) was added to a solution of 1,2,3,4-tetrahydro-benzo[4,5]thieno[2,3-c]pyridine hydrochloride (230 mg) and triethylamine (0.30 ml) in dichloromethane (20 ml) and the reaction stirred at room temperature for 18 h. The mixture was washed with water (30 ml) and brine (20 ml), dried (MgSO$_4$), filtered and evaporated under reduced pressure to give the title compound (180 mg) in crude form.

R$_f$ 0.75 (diethyl ether).

EXAMPLE 1

3-Methyl-2-(1,3,4,9-tetrahydro-β-carboline-2-sulfonylmethyl)-butyric Acid

A solution of 2-chlorosulfonylmethyl-3-methylbutyric acid tert-butyl ester (271 mg) in dichloromethane (5 ml) was added to a mixture of 1,2,3,4-tetrahydro-9H-pyrido[3,4-b]indole (172 mg) and triethylamine (0.42 ml) in dichloromethane (10 ml) at room temperature. The mixture was stirred for 2 h before addition of trifluoroacetic acid (2.4 ml), and stirring continued for a further 2 h. The mixture was evaporated to dryness and the residue partitioned between 1M aqueous sodium hydroxide (15 ml) and diethyl ether (15 ml). The organics were extracted with 1M sodium hydroxide (15 ml). The combined aqueous portions were acidified to pH=5 with 10% citric acid and extracted with ethyl acetate (4×20 ml). The combined organics were washed with water (2×10 ml) and brine (10 ml), then dried (MgSO$_4$), filtered and the solvent removed under reduced pressure to give, after chromatography (SiO2, 20:1 dichloromethane-methanol), the title compound (66 mg, 19%) as a white foam.

R$_f$ 0.45 (10:1 dichloromethane-methanol).

EXAMPLE 2

2-(6-Methoxy-1,3,4,9-tetrahydro-β-carboline-2-sulfonylmethyl)-3-methyl-butyric Acid Trifluoroacetic acid (1 ml) was added to a solution of 2-(6-methoxy-1,3,4,9-tetrahydro-β-carboline-2-sulfonylmethyl)-3-methyl-butyric acid tert-butyl ester (237 mg) in dichloromethane (10 ml) at room temperature under nitrogen. The mixture was stirred for 2 h before being evaporated under reduced pressure. The residue was partitioned between 1M aqueous sodium hydroxide (15 ml) and diethyl ether (15 ml). The organics were extracted with 1M aqueous sodium hydroxide (15 ml). The combined aqueous portions were acidified to pH=5 with 10% citric acid and extracted with ethyl acetate (4×20 ml). The combined organics were washed with water (2×10 ml) and brine (10 ml), then dried (MgSO$_4$), filtered and the solvent removed under reduced pressure to give, after chromatography (SiO$_2$, 20:1 dichloromethane-methanol), the title compound (128 mg, 62%) as a white foam.

R$_f$ 0.56 (10% methanol in dichloromethane). MS(M+1) 381.

The following compounds were prepared in a similar manner:

EXAMPLE 3

2-(3,4-Dihydro-1H-benzo[4,5]furo[2,3-c]pyridine-2-sulfonylmethyl)-3-methyl-butyric Acid From 2-(3,4-dihydro-1H-benzo[4,5]furo[2,3-c]pyridine-2-sulfonylmethyl)-3-methyl-butyric acid tert-butyl ester (610 mg) to give, after chromatography (SiO$_2$, 2.5% dichloromethane in methanol), the title compound (308 mg, 58%) as a white foam.

R$_f$ 0.58 (5% methanol in dichloromethane). MS (M+1) 352 (M−1) 350.

EXAMPLE 4

2-[2-(1-Benzyloxycarbonyl-piperidin4-yl)-2-carboxy-ethanesulfonyl]-1,2,3,4-tetrahydro-β-carboline-9-carboxylic Acid2,2,2-Trichloro-ethyl Ester Prepared from 2-[2-(1-benzyloxycarbonyl-piperidin-4-yl)-2-tert butoxy carbonyl-ethanesulfonyl]-1,2,3,4-tetrahydro-β-carboline-9-carboxylic acid 2,2,2-trichloro-ethyl ester (600 mg) to give, after chromatography (SiO$_2$, 2.5% methanol in dichloromethane), the title compound (530 mg, 94%) as a pale yellow solid.

R$_f$ 0.28 (5% methanol in dichloromethane); $^1$HNMR (400 MHz, d$^6$ DMSO): 8.3 (1H, d), 7.65 (1H, d), 7.5–7.3 (7H, m), 5.3 (2H, s), 5.15 (2H, s), 4.8 (2H, dd), 4.1 (2H br d), 3.65 (2H, m), 3.6–3.35 (3H, m), 2.9–2.77 (4H, m), 1.9 (1H, m), 1.7 (1H, m), 1.6 (1H, m), 1.3–1.1 (2H, m).

EXAMPLE 5

4-(1,3,4,9-Tetrahydro-β-carboline-2-sulfonylmethyl)-tetrahydro-pyran-4-carboxylic Acid 2-(4-Methoxycarbonyl-tetrahydro-pyran-4-ylmethanesulfonyl)-1,2,3,4-tetrahydro-β-carboline-9- carboxylic acid 2,2,2-trichloro-ethyl ester (556 mg) and lithium hydroxide monohydrate (206 mg) in tetrahydrofuran (10 ml), methanol (10 ml) and water (10 ml) was heated to reflux for 8 h. The reaction was left to stand at room temperature overnight and then refluxed for a further 4 h. The mixture was evaporated under reduced pressure and the residue dissolved in water (25 ml) and washed with ethyl acetate (2×30 ml). The aqueous was acidified to pH =4 with 5% citric acid solution and extracted with dichloromethane (2×40 ml) followed by ethyl acetate (3×50 ml). The combined extracts were dried (MgSO$_4$) and evaporated under reduced pressure to give the title compound (299 mg, 80%) as a white solid.

R$_f$ 0.22 (5% methanol in dichloromethane); $^1$HNMR (400 MHz, d$^6$ DMSO): 12.85 (1H, br s), 10.9 (1H, br s), 7.4 (1H, d), 7.3 (1H, d), 7.05 (1H, t), 6.95 (1H, t), 4.45 (2H, br s), 3.75 (2H, m), 3.4 (4H, m), 3.35 (2H, m), 2.8 (2H, m), 2.0 (2H, m), 1.7 (2H, m).

EXAMPLE 6

2-(R)-(3,4-Dihydro-1H-benzo[4,5]thieno[2,3-c]pyridine-2-sulfonylmethyl)-3-methyl-butyric Acid Hydrogen peroxide (30% aqueous, 0.15 ml) was added to a solution of 4(R)-benzyl-3-[2-(R)-(3,4-dihydro-1H-benzo[4,5]thieno[2,3-c]pyridine-2-sulfonylmethyl)-3-methyl-butanoyl]-oxazolidin-2-one (180 mg) in tetrahydrofuran (5 ml) at 0° C., followed by a solution of lithium hydroxide monohydrate (30 mg) in water (3 ml). The reaction was stirred for 16 h, allowing to warm slowly to room temperature. A solution of sodium sulfite (200 mg) in water (5 ml) was added then the mixture was evaporated under reduced pressure. The aqueous residue was washed with diethyl ether (20 ml), acidified with citric acid and extracted with ethyl acetate (2×30 ml). The combined extracts were washed with brine (30 ml), dried (MgSO$_4$), filtered and evaporated under reduced pressure to give the title compound (110 mg) in crude form.

R$_f$ 0.55 (ethyl acetate).

EXAMPLE 7

4-(3,4-Dihydro-1H-benzo[4,5]thieno [2,3-c]pyridine-2-sulfonylmethyl)-tetrahydro-pyran-4-carboxylic Acid 4-Chlorosulfonylmethyl-tetrahydro-pyran-4-carboxylic acid methyl ester (520 mg) was added to a solution of 1,2,3,4-tetrahydrobenzo[4,5]thieno[2,3-c]pyridine hydrochloride (450 mg) and triethlyamine (1.0 ml) in tetrahydrofuran (20 ml). The mixture was stirred at room temperature for 18 h then water (5 ml), methanol (5 ml) and lithium hydroxide monohydrate (400 mg) were added and the reaction heated to reflux for 3 h. The mixture was evaporated under reduced pressure and the aqueous residue washed with diethyl ether (2×10 ml), acidified with 1M hydrochloric acid and the precipitate collected by filtration to give the title compound (200 mg, 25%) as a white solid.

R$_f$ 0.62 (ethyl acetate).

EXAMPLE 8

2-[2-(1-Benzyloxycarbonyl-piperidin-4-yl)-2-hydroxycarbamoyl-ethanesulfonyl]-1,2,3,4-tetrahydro-β-carboline-9-carboxylic Acid 2,2,2-Trichloro-ethyl Ester Oxalyl chloride (0.1 ml) was added to a suspension of 2-[2-(1-benzyloxycarbonyl-piperidin-4-yl)-2-carboxyethanesulfonyl]-1,2,3,4-tetrahydro-β-carboline-9-carboxylic acid 2,2,2-trichloroethyl ester (530 mg) in dichloromethane (10 ml) under nitrogen. N,N-dimethylformamide (a few drops, catalytic) was added and the reaction stirred at room temperature for 1 h. The mixture was evaporated under reduced pressure and the residue suspended in tetrahydrofuran (15 ml). Aqueous hydroxylamine (50% wt solution, 1.5 ml) was added and the reaction stirred for 45 min. The solvent was removed under reduced pressure and the residue purified by chromatography (SiO$_2$, 2.5% methanol in dichloromethane), to give the title compound (147 mg, 27%) as a white solid.

R$_f$ 0.31 (5% methanol in dichloromethane).

EXAMPLE 9

N-Hydroxy-3-methyl-2-(1,3,4,9-tetrahydro-β-carboline-2-sulfonylmethyl)-butyramide Oxalyl chloride (0.2 ml) was added to a slurry of 3-methyl-2-(1,3,4,9-tetrahydro-β-carboline-2-sulfonylmethyl)butyric acid (66 mg) in dichloromethane (10 ml) under nitrogen at room temperature. N,N-dimethylformamide (2 drops) was added, and the mixture stirred for 1 h. The solvent was removed under reduced pressure, and the residue dissolved in tetrahydrofuran (10 ml). A 50% solution of hydroxylamine in water (0.2 ml) was added, and the mixture stirred for 1 h. The reaction mixture was diluted with water (20 ml) and extracted with ethyl acetate (3×10 ml). The combined organics were washed with water (20 ml) and brine (20 ml) before being dried (MgSO$_4$), filtered, evaporated and chromatographed (SiO$_2$, 10% methanol in dichloromethane) to give the title compound (41 mg, 59%) as an off white solid.

R$_f$ 0.53 (10% methanol in dichloromethane); MS 365 (M$^+$).

The following compounds were prepared in a similar manner:

EXAMPLE 10

2-(3,4-Dihydro-1H-benzo[4,5]furo[2,3-c]pyridine-2-sulfonylmethyl)-N-hydroxy-3-methylbutyramide From 2-(3,4-dihydro-1H-benzo[4,5]furo[2,3-c]pyridine-2-sulfonylmethyl)-3-methylbutyric acid (279 mg) to give the title compound (232 mg, 57%) as a white solid.

R$_f$ 0.50 (5% methanol in dichloromethane); MS 366 (M$^+$).

EXAMPLE 11

(1,3,4,9-Tetrahydro-β-carboline-2-sulfonylmethyl)-tetrahydro-pyran-4carboxylic Acid Hydroxamide Prepared from 4-(1,3,4,9-tetrahydro-β-carboline-2-sulfonylmethyl)-tetrahydro-pyran-4-carboxylic acid (296 mg), with purification by reverse phase preparative HPLC using a 25 cm×21.4 mm Phenomenex Luna C18 (2) (5u) column and a mobile phase of aqueous trifluoroacetic acid (0.05% v/v) and acetonitrile under gradient conditions from 15% to 65% acetonitrile. The title compound (77 mg, 25%) was obtained as a white solid, >99% pure by HPLC analysis.

R$_f$ 0.36 (10% methanol in dichloromethane); MS 392 (M−1).

EXAMPLE 12

2-(R)-(3,4-Dihydro-1H-benzo[4,5]thieno[2,3-c]pyridine-2-sulfonylmethyl)-N-hydroxy-3-methyl-butyramide Prepared from 2-(R)-(3,4-dihydro-1H-benzo[4,5]thieno[2,3-c]pyridine-2-sulfonylmethyl)-3-methyl-butyric acid (100 mg) to give, after chromatography (SiO$_2$, 6% methanol in dichloromethane), the title compound (35 mg, 34%) as a beige solid.

R$_f$ 0.44 (6% methanol in dichloromethane); MS 383 (M$^+$).

EXAMPLE 13

4(3,4-Dihydro-1H-benzo[4,5]thieno[2,3-c]pyridine-2-sulfonylmethyl)-tetrahydro-pyran-4-carboxylic Acid Hydroxamide Prepared from 4-(3,4-dihydro-1H-benzo[4,5]thieno[2,3-c]pyridine-2-sulfonylmethyl)tetrahydropyran-4-carboxylic acid (200 mg) to give the title compound (85 mg, 41%) as a beige solid.

R$_f$ 0.35 (6% methanol in dichloromethane); MS 410 (M$^+$).

EXAMPLE 14

N-Hydroxy-2-(6-methoxy-1,3,4,9-tetrahydro-β-carboline-2-sulfonylmethyl)-3-methylbutyramide 1-(3-Dimethylaminopropyl)-3-ethyl carbodiimide hydrochloride (104 mg) was added to a slurry of 2-(6-methoxy-1,3,4,9-tetrahydro-β-carboline-2-sulfonylmethyl)-3-methylbutyric acid (172 mg) in dichloromethane (10 ml). The mixture was stirred for 5 minutes before addition of O-(t-butyldimethylsilyl)hydroxylamine (80 mg), then for 1.5 h. The mixture was poured into water (10 ml) and extracted with dichloromethane (3×15 ml). The combined organics were washed with water (2×50 ml), dried (MgSO$_4$) and evaporated under reduced pressure. The residue was dissolved in dichloromethane (10 ml) and 1.0N hydrogen chloride in ether (2.5 ml) was added. The mixture was stirred at room temperature for 2 h. It was evaporated under reduced pressure and the residue chromatographed (SiO$_2$, 5% methanol in dichloromethane) to give the title compound (37 mg, 21%) as a pale orange solid.

R$_f$ 0.43 (10% methanol in dichloromethane); MS 395 (M$^+$).

EXAMPLE 15

4-[1-Hydroxycarbamoyl-2-(1,3,4,9-tetrahydro-β-carboline-2-sulfonyl)-ethyl]-piperidine-1-carboxylic Acid Benzyl Ester 2-[2-(1-Benzyloxycarbonyl-piperidin-4-yl)-2-hydroxycarbamoyl-ethane sulfonyl]-1,2,3,4-tetrahydro-β-carboline-9-carboxylic acid 2,2,2-trichloro-ethyl ester (135 mg) and 0.1N sodium hydroxide (4.2 ml) in methanol were stirred at room temperature for 3.5 h. The methanol was removed under reduced pressure and the residue partitioned between dichloromethane (20 ml) and 5% citric acid solution (5 ml). The aqueous was extracted with 10% methanol in dichloromethane (2×20 ml) and the combined organics washed with water (2×30 ml) and evaporated under reduced pressure to give the title compound (82 mg, 80%) as a white solid.

R$_f$ 0.30 (10% methanol in dichloromethane); MS 541 (M+1).

We claim:

1. A compound of formula (I)

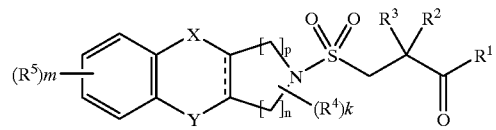

wherein

R$^1$ is OH or NHOH;

R$^2$ is H, alkyl, alkenyl, alkynyl, aryl, arylalkyl, cycloalkyl, or cycloalkylalkyl;

R$^3$ is H or alkyl;

R$^4$ is alkyl, cycloalkyl, OR$^9$, CO$_2$R$^{14}$, COR$^{10}$, S(O)$_q$R$^{10}$ where q is 0, 1 or 2, CONR$^7$R$^8$, CN or S(O)$_q$NR$^7$R$^8$; two R$^4$ substituents may be attached to the same carbon atom to form C(R$^4$)$_2$, where each R$^4$ is the same or different, or C(R$^4$)$_2$ may represent C=O;

R$^5$ is alkyl, cycloalkyl, aryl, CF$_3$, OR$^9$, COR$^{10}$, S(O)$_q$R$^8$, CO$_2$R$^{14}$, CONR$^7$R$^8$, S(O)$_q$NR$^7$R$^8$, halogen, NR$^{10}$R$^{11}$ or CN;

R$^7$ and R$^8$, which may the same or different, are each H, alkyl, cycloalkyl, aryl, arylalkyl, or cycloalkylalkyl;

R$^9$ is H, alkyl, CF$_3$, CH$_2$, CH$_2$F, cycloalkyl, aryl, arylalkyl, or cycloalkylalkyl;

R$^{10}$ is H, alkyl, cycloalkyl, aryl, arylalkyl, or cycloalkylalkyl; and

R$^{11}$ is H, alkyl, cycloalkyl, aryl, arylalkyl, cycloalkylalkyl, COR$^{12}$, CONR$^7$R$^8$, S(O)$_q$R$^{12}$ or S(O)$_q$NR$^7$R$^8$;

R$^{12}$ is OR$^9$ or R$^{13}$;

R$^{13}$ is alkyl, cycloalkyl, aryl, arylalkyl, or cycloalkylalkyl;

R$^{14}$ is H, alkyl or cycloalkyl;

X is —O—, —N—, —N(R$^{11}$)—, or S(O)$_q$ where q is 0 or 2;

----- represents a single or double bond;

each k and m is independently 0, 1, 2 or 3;

n is 1 or 2; and is 1 or 2, provided that n+p is 3;

or a salt, solvate, hydrate, N-oxide, protected amino, protected carboxy or protected hydroxamic acid thereof.

2. The compound of claim 1, wherein R$^1$ is NHOH.

3. The compound of claim 1, wherein p is 1; R$^4$ is alkyl, cycloalkyl, OR$^9$, CO$_2$R$^{14}$, COR$^{10}$, S(O)$_q$R$^{10}$, CONR$^7$R$^8$, CN, or S(O)$_q$NR$^7$R$^8$, or C(R$^4$)$_2$ may represent C=O; and n is 2.

4. The compound of claim 1, which is selected from 3-methyl-2-(1,3,4,9-tetrahydro-β-carboline-2-sulfonylmethyl)butyric acid, 2-(6-methoxy-1,3,4,9-tetrahydro-β-carboline-2-sulfonylmethyl)-3-methylbutyric acid, 2-(3,4-dihydro-1H-benzo[4,5]furo[2,3-c]pyridine-2-sulfonylmethyl)-3-methylbutyric acid, N-hydroxy-3-methyl-2-(1,3,4,9-tetrahydro-β-carboline-2-sulfonylmethyl)-butyramide, 2-(3,4-dihydro-1H-benzo[4,5]furo[2,3-c]pyridine-2-sulfonylmethyl-N-hydroxy-3-methylbutyramide, and
N-hydroxy-2-(6-methoxy-1,3,4,9-tetrahydro-β-carboline-2-sulfonylmethyl)-3-methylbutyramide.

5. The compound of claim 1, which is selected from
2-(R)-(3,4-dihydro-1H-benzo[4,5]thieno[2,3-c]pyridine-2-sulfonylmethyl-3-methylbutyric acid, and
2-(R)-(3,4-dihydro-1H-benzo[4,5]thieno[2,3 -c]pyridine-2-sulfonylmethyl-N-hydroxy-3-methylbutyramide.

6. A pharmaceutical composition for use in therapy, comprising a compound of formula (I)

wherein
$R^1$ is OH or NHOH;
$R^2$ is H, alkyl, alkenyl, alkynyl, aryl, arylalkyl, cycloalkyl, or cycloalkylalkyl;
$R^3$ is H or alkyl;
$R^4$ is alkyl, cycloalkyl, $OR^9$, $CO_2R^{14}$, $COR^{10}$, $S(O)_qR^{10}$ where q is 0, 1 or 2, $CONR^7R^8$, CN or $S(O)_qNR^7R^8$; two $R^4$ substituents may be attached to the same carbon atom to form $C(R^4)_2$, where each $R^4$ is the same or different, or $C(R^4)_2$ may represent C=O;
$R^5$ is alkyl, cycloalkyl, aryl, $CF_3$, $OR^9$, $COR^{10}$, $S(O)_qR^{10}$, $CO_2R^{14}$, $CONR^7R^8$, $S(O)_qNR^7R^8$, halogen, $NR^{10}OR^{11}$ or CN;
$R^7$ and $R^8$, which may the same or different, are each H, alkyl, cycloalkyl, aryl, arylalkyl, or cycloalkylal;
$R^9$ is H, alkyl, $CF_3$, $CHF_2$, $CH_2F$, cycloakyl, aryl, arylalkyl, or cycloalkylalkyl;
$R^{10}$ is H, alkyl, cycloalkyl, aryl, arylalkyl, or cycloalkylalkyl; and
$R^{11}$ is H, alkyl, cyctoalkyl, aryl, arylalkyl, cycloalkylalkyl, $COR^{12}$, $CONR^7R^8$, $S(O)_qR^{12}$ or $S(O)_qNR^7R^8$;
$R^{12}$ is $OR^9$ or $R^3$;
$R^{13}$ is alkyl, cycloalkyl, a&yl, arylalkyl, or cycloalkylalkyl;
$R^{14}$ is H, alkyl or cycloalkyl;
X is —O—, —N—, —N($R^{11}$)—, or $S(O)_q$ where q is 0 or 2;

----- represents a single or double bond;
each k and m is independently 0, 1, 2 or 3;
n is 1 or 2; and
p is 1 or 2, provided that n+p is 3;
or a salt, solvate, hydrate, N-oxide, protected amino, protected carboxy or protected hydroxamic acid thereof;
and a pharmaceutically-acceptable diluent or carrier.

7. The composition of claim 6, wherein wherein $R^1$ is NHOH.

8. The composition of claim 6, wherein p is 1; $R^4$ is alkyl, cycloalkyl, $OR^9$, $CO_2R^{14}$, $COR^{10}$, $S(O)_qR^{10}$, $CONR^7R^8$, CN, or $S(O)_qNR^7R^8_3$ or $C(R^4)_2$ may represent CO; and n is 2.

9. The composition of claim 6, wherein said compound is selected from
3-methyl-2-(1,3,4,9-tetrahydro-β-carboline-2-sulfonylmethyl)butyric acid,
2-(6-methoxy-1,3,4,9-tetrahydro-β-carboline-2-sulfonylmethyl)-3-methylbutyric acid,
2-(3,4-dihydro-1H-benzo[4,5]furo[2,3-c]pyridine-2-sulfonylmethyl)-3-methylbutyric acid,
N-hydroxy-3-methyl-2-(1,3,4,9-tetrahydro-β-carboline-2-sulfonylmethyl)-butyramide,
2-(3,4-dihydro-1H-benzo[4,5]furo[2,3-c]pyridine-2-sulfonylmethyl-N-hydroxy-3-methylbutyramide, and
N-hydroxy-2-(6-methoxy-1,3,4,9-tetrahydro-β-carboline-2-sulfonylmethyl)-3-methylbutyramide.

10. The composition of claim 6, wherein said compound is selected from
2-(R)-(3,4-dihydro-1H-benzo[4,5]thieno[2,3 -c]pyridine-2-sulfonylmethyl-3-methylbutyric acid, and
2-(R)-(3,4-dihydro-1H-benzo[4,5]thieno[2,3-c]pyridine-2-sulfonylmethyl-N-hydroxy-3-methylbutyramide.

11. A method for the treatment of inflammation; wherein said method comprises administering to a patient in need of such treatment an effective amount of a compound of formula (I)

wherein
$R^1$ is OH or NHOH;
$R^2$ is H, alkyl, alkenyl, alkynyl, aryl, arylalkyl, cycloalkyl, or cycloalkylalkyl;
$R^3$ is H or alkyl;
$R^4$ is alkyl, cycloalkyl, $OR^9$, $CO_2R^{14}$, $COR^{10}$, $S(O)_qR^{10}$ where q is 0, 1 or 2, $CONR^7R^8$, CN $S(O)_qNR^7R^8$; two $R^4$ substituents may be attached to the same carbon atom to form $C(R^4)_2$, where each $R^4$ is the same or different, or $C(R^4)_2$ may represent C=O;
$R^5$ is alkyl, cycloalkyl, aryl, $CF_3$, $OR^9$, $COR^{10}$, $S(O)_qR^{10}$, $CO_2R^{14}$, $CONR^7R^8$, $S(O)_qNR^7R^8$, halogen, $NR^{10}R^{11}$ or CN;
$R^7$ and $R^8$, which may the same or different, are each H, alkyl, cycloalkyl, aryl, arylalkyl, or cycloalkylalkyl;
$R^9$ is H, alkyl, $CF_3$, $CBF_2$, $CH_2F$, cycloalkyl, aryl, arylalkyl, or cycloalkylalkyl;
$R^{10}$ is H, alkyl, cycloalkyl, aryl, arylalkyl, or cycloalkylalkyl; and
$R^{11}$ is H, alkyl, cycloalkyl, aryl, arylalkyl, cycloalkylal, $COR^{12}$, $CONR^7R^8$, $S(O)_qR^{12}$ or $S(O)_qNR^7R^8$;
$R^{12}$ is $OR^9$ or $R^3$;
$R^{13}$ is alkyl, cycloalkyl, aryl, arylalkyl or cycloalkylalkyl;
$R^{14}$ is H, alkyl or cycloalkyl;
X is —O—, —N—, —N($R^{11}$)—, or $S(O)_q$ where q is 0 or 2;

represents a single or double bond;

each k and m is independently 0, 1, 2 or 3;

n is 1 or 2; and p is 1 or 2, provided that n+p is 3;

or a salt, solvate, hydrate, N-oxide, protected amino, protected carboxy or protected hydroxamic acid thereof.

12. The method of claim 11, wherein wherein $R^1$ is NHOH.

13. The method of claim 11, wherein p is 1; $R^4$ is alkyl, cycloalkyl, $OR^9$, $CO_2R^{14}$, $COR^{10}$, $S(O)_qR^{10}$, $CONR^7R^8$, CN, or $S(O)_qNR^7R^8$, or $C(R^4)_2$ may represent C=O; and n is 2.

14. The method of claim 11, wherein said compound is selected from 3-methyl-2-(1,3,4,9-tetrahydro-β-carboline-2-sulfonylmethyl)butyric acid, 2-(6-methoxy-1,3,4,9-tetrahydro-β-carboline-2-sulfonylmethyl)-3-methylbutyric acid, 2-(3,4-dihydro-1H-benzo[4,5]furo[2,3-c]pyridine-2-sulfonylmethyl)-3-methylbutyric acid, N-hydroxy-3-methyl-2-(1,3,4,9-tetrahydro-β-carboline-2-sulfonylmethyl)-butyramide, 2-(3,4-dihydro-1H-benzo[4,5]furo[2,3-c]pyridine-2-sulfonylmethyl-N-hydroxy-3-methylbutyramide, and N-hydroxy-2-(6-methoxy-1,3,4,9-tetrahydro-β-carboline-2-sulfonylmethyl)-3-methylbutyramide.

15. The method of claim 11, wherein said compound is selected from 2-(R)-(3,4-dihydro-1H-benzo[4,5]thieno[2,3-c]pyridine-2-sulfonylmethyl-3-methylbutyric acid, and 2-(R)-(3,4-dihydro-1H-benzo[4,5]thieno[2,3 -c]pyridine-2-sulfonylmethyl-N-hydroxy-3-methylbutyramide.

* * * * *